US010668097B1

(12) United States Patent
Jones

(10) Patent No.: US 10,668,097 B1
(45) Date of Patent: Jun. 2, 2020

(54) TESTOSTERONE ENHANCING COMPOSITIONS AND METHODS

(71) Applicant: Direct Digital LLC, Charlotte, NC (US)

(72) Inventor: Natalie Jones, Charlotte, NC (US)

(73) Assignee: DIRECT DIGITAL, LLC, Charlotte, NC (US)

( * ) Notice: Subject to any disclaimer, the term of this patent is extended or adjusted under 35 U.S.C. 154(b) by 0 days.

(21) Appl. No.: 16/360,336

(22) Filed: Mar. 21, 2019

(51) Int. Cl.

| | |
|---|---|
| *A61K 31/714* | (2006.01) |
| *A61K 47/02* | (2006.01) |
| *A61K 47/12* | (2006.01) |
| *A61K 47/46* | (2006.01) |
| *A61K 36/48* | (2006.01) |
| *A61K 31/4415* | (2006.01) |
| *A61K 33/30* | (2006.01) |
| *A61K 31/198* | (2006.01) |
| *A61K 35/10* | (2015.01) |
| *A61K 36/73* | (2006.01) |
| *A61K 31/69* | (2006.01) |

(52) U.S. Cl.
CPC .......... *A61K 31/714* (2013.01); *A61K 31/198* (2013.01); *A61K 31/4415* (2013.01); *A61K 31/69* (2013.01); *A61K 33/30* (2013.01); *A61K 35/10* (2013.01); *A61K 36/48* (2013.01); *A61K 36/73* (2013.01); *A61K 47/02* (2013.01); *A61K 47/12* (2013.01); *A61K 47/46* (2013.01)

(58) Field of Classification Search
None
See application file for complete search history.

(56) References Cited

U.S. PATENT DOCUMENTS

| | | | |
|---|---|---|---|
| 8,846,061 B1 * | 9/2014 | Bezzek | A61K 31/122 424/400 |
| 9,216,184 B1 | 12/2015 | Trunin et al. | |
| 9,561,175 B1 | 2/2017 | Menegan et al. | |
| 2007/0224302 A1 * | 9/2007 | Talbot | A61K 36/185 424/773 |
| 2014/0335153 A1 | 11/2014 | Allen et al. | |
| 2017/0151271 A1 | 6/2017 | Paxton-Pierson | |

FOREIGN PATENT DOCUMENTS

KR 101579845 B1 12/2015

OTHER PUBLICATIONS

Joy (BMC Complementary and Alternative Medicine (2016), 16:224).*
"Nugenix Review" (Internet Archived version from Mar. 8, 2018: https://web.archive.org/web/20180308223529/https://thesupplementreviews.org/testosterone-boosters/nugenix-review/ ).*
Balliett et al.; "Changes in anthropometric measurements, body composition, blood pressure, lipid profile, and testosterone in patients participating in a low-energy dietary intervention"; Journal of Chiropractic Medicine (2013) 12; pp. 3-14 (12 pages).
Force Factor; Force Factor Introduces Text X180 Tempest for Unparalleled Athleticism; NutraClick®; retrieved online May 9, 2018 (2 pages).
Nugenix Testosterone Booster; Hugely Popular but Is it Effective?; Nugenix includes Fenugreek Extract, Citrulline Malate, and Tribulus; https://thesupplementreviews.org/testosterone-boosters/nugenix-review/; retrieved online May 9, 2018 (5 pages).
Tribulean Alpha; Strongest Testosterone Booster for Men (2100mg+), Natural Testosterone Booster: Fast Acting Fenugreek, Tribulus Terrestris, L-Citruline, L-Arginine, Maca, Boron, L-Carnitine by Engineered Evolution; retrieved online May 9, 2018 (4 pages).

* cited by examiner

*Primary Examiner* — Susan Hoffman
(74) *Attorney, Agent, or Firm* — Venable LLP; Jeffri A. Kaminski

(57) ABSTRACT

A composition for the enhancement of free testosterone is provided, the composition comprising: vitamin B6; vitamin B12; zinc; L-citrulline; fenugreek seed extract; an adenosine triphosphate (ATP) stimulating component, comprising: ancient peat extract, and apple fruit extract; eurycoma root extract; and boron. A method of increasing free testosterone is provided, the method comprising administering to an individual an effective dose of a composition comprising: vitamin B6; vitamin B12; zinc; L-citrulline; fenugreek seed extract; an adenosine triphosphate (ATP) stimulating component, comprising: ancient peat extract, and apple fruit extract; eurycoma extract; and boron.

19 Claims, No Drawings

TESTOSTERONE ENHANCING COMPOSITIONS AND METHODS

TECHNICAL FIELD

The present invention generally relates to compositions and methods for enhancing free testosterone. In particular, the invention is a composition and method of enhancing testosterone by administering novel nutraceutical compositions.

BACKGROUND

Free testosterone is essential for good health and vitality. However, as men age, free testosterone levels decline, resulting in increased fatigue, decrease in athletic performance, decrease in power, inability to focus, decrease in muscle tone, decrease in stamina, and decreased libido. There is a need for a natural and effective method of safely increasing free testosterone levels.

SUMMARY

According to an embodiment, a composition for the enhancement of free testosterone is provided, the composition comprising: vitamin B6; vitamin B12; zinc; L-citrulline; fenugreek seed extract; an adenosine triphosphate (ATP) stimulating component, comprising: ancient peat extract, and apple fruit extract; *Eurycoma longifolia* (longjack) root extract; and boron.

According to another embodiment, a method of increasing free testosterone is provided, the method comprising administering to an individual an effective dose of a composition comprising: vitamin B6; vitamin B12; zinc; L-citrulline; fenugreek seed extract; an adenosine triphosphate (ATP) stimulating component, comprising: ancient peat extract, and apple fruit extract; eurycoma root extract; and boron.

According to another embodiment, the use of a composition increasing testosterone in the preparation of medicament for the treatment of a testosterone mediated disorder is provided, the composition comprising: vitamin B6; vitamin B12; zinc; L-citrulline; fenugreek seed extract; an adenosine triphosphate (ATP) stimulating component, comprising: ancient peat extract, and apple fruit extract; eurycoma root extract; and boron.

DETAILED DESCRIPTION

Embodiments of the invention are discussed in detail below. In describing embodiments, specific terminology is employed for the sake of clarity. A person skilled in the relevant art will recognize that other equivalent parts can be employed and other methods developed without departing from the spirit and scope of the invention.

Described herein are therapeutic compositions comprising mixtures of testosterone boosting ingredients, and methods of treating testosterone mediated disorders comprising administering an effective amount of a therapeutic composition.

In one aspect, described herein is a therapeutic composition comprising at least one testosterone boosting ingredient, and an adenosine triphosphate (ATP) stimulating component. ATP is a molecule that provides energy to drive many processes in living cells, such as muscle contraction. Increasing ATP production in vivo is thought to correlate with better overall health and athletic performance, among other improvements.

According to embodiments, the testosterone boosting ingredient comprises at least one of an amino acid, vitamin B6, vitamin B12, vitamin D, *Tribulus terrestris* and extracts thereof, fenugreek seed and extracts thereof, *Eurycoma longifolia* and extracts thereof, zinc, and boron. According to embodiments, the amino acid may be L-citrulline, L-arginine, D-aspartic acid, or leucine. According to embodiments, the fenugreek seed extract may comprise Testofen® (GE Nutrients, Irvine, Calif.).

According to embodiments, the ATP stimulating component may be comprised of at least one of ancient peat and extracts thereof, apple fruit and extracts thereof, or a combination thereof. According to embodiments, ancient peat extract may be extracted from, for example, fossilized plant material. According to embodiments, the ATP stimulating component may comprise elevATP® (Futureceuticals, Momence, Ill.).

In another aspect, described herein is a composition comprising:
(a) at least one testosterone boosting ingredient;
(b) an ATP stimulating component;
(c) at least one excipient; and
(d) a capsule.

In some embodiments, the excipient may be a coloring agent. In some embodiments, the excipient may be a diluent. In some embodiments, the excipient may be a binder. In some embodiments, the excipient may be a granulating agent. In some embodiments, the excipient may be a bulking agent. In some embodiments, the excipient may be a disintegrant. In some embodiments, the excipient may be a glidant. In some embodiments, the excipient may be a flavorant. In some embodiments, the excipient may be a buffer. In some embodiments, the excipient may be a surfactant. In some embodiments, the excipient may be a stabilizer. In some embodiments, the excipient is selected from sugars, starches, polymers, alkaline and/or alkali earth stearate, carbonate and/or sulfate, kaolin, silica, flavorants, and aromas, and combinations of any thereof. In some embodiments, the excipient may be lipophilic, polymeric, cellulosic or combinations of any thereof. In some embodiments, the excipient may be selected from lactose, magnesium stearate, sodium carbonate, microcrystalline cellulose, silica, titanium dioxide, rice flour, and combinations of any thereof. According to embodiments, the composition may be encapsulated. According to embodiments, the capsule may be a gelatin capsule.

In some embodiments, the amount of vitamin B6 is about 0.1 mg, about 0.2 mg, about 0.3 mg, about 0.4 mg, about 0.5 mg, about 0.6 mg, about 0.7 mg, about 0.8 mg, about 0.9 mg, about 1.0 mg, about 1.1 mg, about 1.2 mg, about 1.3 mg, about 1.4 mg, about 1.5 mg, about 1.6 mg, about 1.7 mg, about 1.8 mg, about 1.9 mg, about 2.0 mg, about 2.1 mg, about 2.2 mg, about 2.3 mg, about 2.4 mg, about 2.5 mg, about 2.6 mg, about 2.7 mg, about 2.8 mg, about 2.9 mg, about 3.0 mg, about 3.1 mg, about 3.2 mg, about 3.3 mg, about 3.4 mg, about 3.5 mg, about 3.6 mg, about 3.7 mg, about 3.8 mg, about 3.9 mg, about 4.0 mg, about 4.1 mg, about 4.2 mg, about 4.3 mg, about 4.4 mg, about 4.5 mg, about 4.6 mg, about 4.7 mg, about 4.8 mg, about 4.9 mg, or about 5.0 mg.

In some embodiments, the amount of vitamin B12 is about 0.1 mcg, about 0.2 mcg, about 0.3 mcg, about 0.4 mcg, about 0.5 mcg, about 0.6 mcg, about 0.7 mcg, about 0.8 mcg, about 0.9 mcg, about 1.0 mcg, about 1.1 mcg, about 1.2 mcg, about 1.3 mcg, about 1.4 mcg, about 1.5 mcg, about 1.6 mcg, about 1.7 mcg, about 1.8 mcg, about 1.9 mcg, about 2.0 mcg, about 2.1 mcg, about 2.2 mcg, about 2.3 mcg, about 2.4 mcg, about 2.5 mcg, about 2.6 mcg, about 2.7 mcg, about 2.8 mcg, about 2.9 mcg, about 3.0 mcg, about 3.1 mcg, about 3.2 mcg, about 3.3 mcg, about 3.4 mcg, about 3.5 mcg, about 3.6 mcg, about 3.7 mcg, about 3.8 mcg, about 3.9 mcg, about 4.0 mcg, about 4.1 mcg, about 4.2 mcg, about 4.3 mcg, about 4.4 mcg, about 4.5 mcg, about 4.6 mcg, about 4.7 mcg, about 4.8 mcg, about 4.9 mcg, or about 5.0 mcg.

In some embodiments, the amount of zinc is about 0.01 mg, about 0.02 mg, about 0.03 mg, about 0.04 mg, about 0.05 mg, about 0.06 mg, about 0.07 mg, about 0.08 mg, about 0.09 mg, about 0.1 mg, about 0.2 mg, about 0.3 mg, about 0.4 mg, about 0.5 mg, about 0.6 mg, about 0.7 mg, about 0.8 mg, about 0.9 mg, about 1.0 mg, about 1.1 mg, about 1.2 mg, about 1.3 mg, about 1.4 mg, about 1.5 mg, about 1.6 mg, about 1.7 mg, about 1.8 mg, about 1.9 mg, about 2.0 mg, about 2.1 mg, about 2.2 mg, about 2.3 mg, about 2.4 mg, about 2.5 mg, about 2.6 mg, about 2.7 mg, about 2.8 mg, about 2.9 mg, about 3.0 mg, about 3.1 mg, about 3.2 mg, about 3.3 mg, about 3.4 mg, about 3.5 mg, about 3.6 mg, about 3.7 mg, about 3.8 mg, about 3.9 mg, about 4.0 mg, about 4.1 mg, about 4.2 mg, about 4.3 mg, about 4.4 mg, about 4.5 mg, about 4.6 mg, about 4.7 mg, about 4.8 mg, about 4.9 mg, or about 5.0 mg.

In some embodiments, the amount of L-citrulline malate is about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, 425 mg, about 450 mg, about 475 mg, 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1025 mg, about 1050 mg, about 1075 mg, about 1100 mg, about 1125 mg, about 1150 mg, about 1175 mg, about 1200 mg, about 1225 mg, about 1250 mg, about 1275 mg, about 1300 mg, about 1325 mg, about 1350 mg, about 1375 mg, about 1400 mg, about 1425 mg, about 1450 mg, about 1475 mg, about 1500 mg, about 1525 mg, about 1550 mg, about 1575 mg, about 1600 mg, about 1625 mg, about 1650 mg, about 1675 mg, about 1700 mg, about 1725 mg, about 1750 mg, about 1775 mg, about 1800 mg, about 1825 mg, about 1850 mg, about 1875 mg, about 1900 mg, about 1925 mg, about 1950 mg, about 1975 mg, about 2000 mg, 2025 mg, 2050 mg, 2075 mg, about 2100 mg, about 2125 mg, about 2150 mg, about 2175 mg, about 2200 mg, about 2225 mg, about 2250 mg, about 2275 mg, or about 2300 mg.

In some embodiments, the amount of fenugreek seed extract is about 25 mg, about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, 425 mg, about 450 mg, about 475 mg, 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1025 mg, about 1050 mg, about 1075 mg, about 1100 mg, about 1125 mg, about 1150 mg, about 1175 mg, about 1200 mg, about 1225 mg, about 1250 mg, about 1275 mg, about 1300 mg, about 1325 mg, about 1350 mg, about 1375 mg, about 1400 mg, about 1425 mg, about 1450 mg, about 1475 mg, or about 1500 mg.

In some embodiments, the amount of ancient peat extract and apple fruit extract combined is about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, 85 mg, about 90 mg, about 95 mg, 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, about 185 mg, about 190 mg, about 195 mg, about 200 mg, 205 mg, about 210 mg, about 215 mg, about 220 mg, about 225 mg, about 230 mg, about 235 mg, about 240 mg, about 245 mg, about 250 mg, about 255 mg, about 260 mg, about 265 mg, about 270 mg, about 275 mg, about 280 mg, about 285 mg, about 290 mg, about 295 mg, about 300 mg, 305 mg, about 310 mg, about 315 mg, about 320 mg, about 325 mg, about 330 mg, about 335 mg, about 340 mg, about 345 mg, about 350 mg, about 355 mg, about 360 mg, about 365 mg, about 370 mg, about 375 mg, about 380 mg, about 385 mg, about 390 mg, about 395 mg, about 400 mg, 405 mg, about 410 mg, about 415 mg, about 420 mg, about 425 mg, about 430 mg, about 435 mg, about 440 mg, about 445 mg, about 450 mg, about 455 mg, about 460 mg, about 465 mg, about 470 mg, about 475 mg, about 480 mg, about 485 mg, about 490 mg, about 495 mg, or about 500 mg.

In some embodiments, the amount of eurycoma root extract is about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, 85 mg, about 90 mg, about 95 mg, 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, about 185 mg, about 190 mg, about 195 mg, about 200 mg, about 205 mg, about 210 mg, about 215 mg, about 220 mg, about 225 mg, about 230 mg, about 235 mg, about 240 mg, about 245 mg, about 250 mg, about 255 mg, about 260 mg, about 265 mg, about 270 mg, about 275 mg, about 280 mg, about 285 mg, about 290 mg, about 295 mg, or about 300 mg.

In some embodiments, the amount of boron is about 0.5 mg, about 0.6 mg, about 0.7 mg, about 0.8 mg, about 0.9 mg, about 1.0 mg, about 1.1 mg, about 1.2 mg, about 1.3 mg, about 1.4 mg, about 1.5 mg, about 1.6 mg, about 1.7 mg, about 1.8 mg, about 1.9 mg, about 2.0 mg, about 2.1 mg, about 2.2 mg, about 2.3 mg, about 2.4 mg, about 2.5 mg, about 2.6 mg, about 2.7 mg, about 2.8 mg, about 2.9 mg, about 3.0 mg, about 3.1 mg, about 3.2 mg, about 3.3 mg, about 3.4 mg, about 3.5 mg, about 3.6 mg, about 3.7 mg, about 3.8 mg, about 3.9 mg, about 4.0 mg, about 4.1 mg, about 4.2 mg, about 4.3 mg, about 4.4 mg, about 4.5 mg, about 4.6 mg, about 4.7 mg, about 4.8 mg, about 4.9 mg, about 5.0 mg, about 5.1 mg, about 5.2 mg, about 5.3 mg, about 5.4 mg, about 5.5 mg, about 5.6 mg, about 5.7 mg, about 5.8 mg, about 5.9 mg, about 6.0 mg, about 6.1 mg, about 6.2 mg, about 6.3 mg, about 6.4 mg, about 6.5 mg, about 6.6 mg, about 6.7 mg, about 6.8 mg, about 6.9 mg, about 7.0 mg, about 7.1 mg, about 7.2 mg, about 7.3 mg, about 7.4 mg, about 7.5 mg, about 7.6 mg, about 7.7 mg, about 7.8 mg, about 7.9 mg, about 8.0 mg, 8.1 mg, about 8.2 mg, about 8.3 mg, about 8.4 mg, about 8.5 mg, about 8.6 mg, about 8.7 mg, about 8.8 mg, about 8.9 mg, about 9.0 mg, about 9.1 mg, about 9.2 mg, about 9.3 mg, about 9.4 mg, about 9.5 mg, about 9.6 mg, about 9.7 mg, about 9.8 mg, about 9.9 mg, about 10.0 mg, about 10.1 mg, about 10.2 mg, about 10.3 mg, about 10.4 mg, about 10.5 mg, about 10.6 mg, about 10.7 mg, about 10.8 mg, about 10.9 mg, about 11.0 mg, about 11.1 mg, about 11.2 mg, about 11.3 mg, about 11.4 mg, about 11.5 mg, about 11.6 mg, about 11.7 mg, about 11.8 mg, about 11.9 mg, about 12.0 mg, about 12.1 mg, about 12.2 mg, about 12.3 mg, about 12.4 mg, about 12.5 mg, about 12.6 mg, about 12.7 mg, about 12.8 mg, about 12.9 mg, about 13.0 mg, about 13.1 mg, about 13.2 mg, about 13.3 mg, about 13.4 mg, about 13.5 mg, about 13.6 mg, about 13.7 mg, about 13.8 mg, about 13.9 mg, about 14.0 mg, about 14.1 mg, about 14.2 mg, about 14.3 mg, about 14.4 mg, about 14.5 mg, about 14.6 mg, about 14.7 mg, about 14.8 mg, about 14.9 mg, about 15.0 mg, about 15.1 mg, about 15.2 mg, about 15.3 mg, about 15.4 mg, about 15.5 mg, about 15.6 mg, about 15.7 mg, about 15.8 mg, about 15.9 mg, about 16.0 mg, about 16.1 mg, about 16.2 mg, about 16.3 mg, about 16.4 mg, about 16.5 mg, about 16.6 mg, about 16.7 mg, about 16.8 mg, about 16.9 mg, about 17.0 mg, about 17.1 mg, about 17.2 mg, about 17.3 mg, about 17.4 mg, about 17.5 mg, about 17.6 mg, about 17.7 mg, about 17.8 mg, about 17.9 mg, about 18.0 mg, about 18.1 mg, about 18.2 mg, about 18.3 mg, about 18.4 mg, about 18.5 mg, about 18.6 mg, about 18.7 mg, about 18.8 mg, about 18.9 mg, about 19.0 mg, about 19.1 mg, about 19.2 mg, about 19.3 mg, about 19.4 mg, about 19.5 mg, about 19.6 mg, about 19.7 mg, about 19.8 mg, about 19.9 mg, about 20.0 mg.

According to an embodiment, the composition may comprise vitamin B6; vitamin B12; zinc; L-citrulline; fenugreek seed extract; an adenosine triphosphate (ATP) stimulating component, comprising: ancient peat extract, and apple fruit extract; eurycoma root extract; and boron.

According to an embodiment, the composition may comprise vitamin B6; vitamin B12; zinc; L-citrulline; fenugreek seed extract; an adenosine triphosphate (ATP) stimulating component, comprising: ancient peat extract, and apple fruit extract; eurycoma root extract; boron, and at least one excipient.

According to an embodiment, the composition may comprise vitamin B6; vitamin B12; zinc; L-citrulline; fenugreek seed extract; an adenosine triphosphate (ATP) stimulating component, comprising: ancient peat extract, and apple fruit extract; eurycoma root extract; boron; rice flour; magnesium stearate; and silica.

According to an embodiment, the composition may comprise at least 0.01% w/w of vitamin B6; at least 0.00001% w/w of vitamin B12; at least 0.01% w/w of zinc; at least 20% w/w of L-citrulline; at least 10% w/w of a fenugreek seed extract; at least 1% w/w of an ATP stimulating component comprising ancient peat extract and apple fruit extract; at least 1% w/w of the eurycoma root extract; and at least 0.1% w/w of boron.

According to an embodiment, the composition may comprise from about 0.01% w/w to about 5% w/w of vitamin B6; from about 0.00001% w/w to about 1% w/w of vitamin B12; from about 0.01% w/w to about 2% w/w of zinc; from about 20% w/w to about 75% w/w of the L-citrulline; from about 10% w/w to about 50% w/w of a fenugreek seed extract; from about 1% w/w to about 20% w/w of an ATP stimulating component comprising ancient peat extract and apple fruit extract; from about 1% w/w to about 20% w/w of the eurycoma root extract; and from about 0.1% w/w to about 2% w/w of boron.

According to an embodiment, the composition may comprise about 0.1% w/w of vitamin B6; about 0.0001% w/w of vitamin B12; about 0.05% w/w of zinc; about 57% w/w of L-citrulline malate; about 30% w/w of a fenugreek seed extract; about 8% w/w of an ATP stimulating component comprising ancient peat extract and apple fruit extract; about 5% w/w of the eurycoma root extract; and about 0.5% w/w of boron.

According to an embodiment, the composition may comprise about 0.67 mg of vitamin B6; about 0.8 mcg of vitamin B12; about 0.33 mg of zinc; about 375 mg of L-citrulline malate; about 200 mg of fenugreek seed extract; about 50 mg of an adenosine triphosphate (ATP) stimulating component, comprising: ancient peat extract, and apple fruit extract; about 100 mg eurycoma root extract; and about 10 mg boron.

According to an embodiment, the composition may comprise about 2 mg of vitamin B6; about 0.0024 mg of vitamin B12; about 1 mg of zinc; about 1125 mg of L-citrulline malate; about 600 mg of fenugreek seed extract; about 150 mg of an adenosine triphosphate (ATP) stimulating component, comprising: ancient peat extract, and apple fruit extract; about 100 mg eurycoma root extract; and about 10 mg boron.

According to embodiments, the composition according to the present invention may be in a capsule. According to embodiments the composition according to the present invention may be administered as an oral dosage form. According to an embodiment, an effective amount may be administered in a single dosage form. According to embodiments, an effective amount may be administered in multiple dosage forms. According to embodiments, the composition according to the present invention may be administered to a male human.

According to embodiments, the composition according to the present invention increases or otherwise enhances circulating free testosterone. According to embodiments, the composition according to the present invention treats testosterone mediated disorders. According to embodiments, the composition according to the present invention increases physical performance. According to embodiments, the composition according to the present invention increases energy level in the individual. According to embodiments, the composition according to the present invention increases stamina in the individual. According to embodiments, the composition according to the present invention increases libido and/or sex drive in the individual. According to embodiments, the composition according to the present invention decreases fatigue in the individual.

EXAMPLES

The following examples are provided for illustrative purposes only, and are intended to be purely exemplary of the disclosure and are not intended to limit the scope of the claims provided herein. Efforts have been made to ensure accuracy with respect to numbers (e.g., amounts, weights, percentages etc.), but some errors and deviations should be accounted for.

TABLE 1

Example 1 Composition

| Amount Per Serving | Dosage | % DV |
|---|---|---|
| Active Ingredients | | |
| Vitamin B6 (as pyridoxine hydrochloride) | 2 mg | 118% |
| Vitamin B12 (as methylcobalamin) | 0.0024 mg | 100% |
| Zinc (as zinc chelate) | 1 mg | 9% |
| L-Citrulline malate (2:1) | 1125 mg | |
| Fenugreek Extract (seed)(50% Fenuside ™)(Testofen ®) | 600 mg | |
| elevATP ® Blend [Ancient Peat Extract (trace minerals) and Apple Fruit Extract] | 150 mg | |
| *Eurycoma longifolia* Extract (root) | 100 mg | |
| Boron (as boron glycinate) | 10 mg | |
| Other Ingredients | | |
| rice flour, magnesium stearate, silica | | |
| Capsule | | |
| gelatin | | |

It is foreseen that the aspects and features of the various embodiments described herein may be used in combination with each other.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

I claim:

1. A composition for the enhancement of free testosterone, comprising:
   vitamin B6;
   vitamin B12;
   zinc;
   L-citrulline;
   fenugreek seed extract;
   an adenosine triphosphate (ATP) stimulating component, comprising:
   ancient peat extract, and
   apple fruit extract;
   eurycoma root extract; and
   boron,
   wherein the composition is in a capsule.

2. The composition of claim 1, further comprising at least one excipient.

3. The composition of claim 2, wherein the excipient is at least one of rice flour, magnesium stearate, silica, and a combination thereof.

4. The composition of claim 1 comprising:
   at least 0.01% w/w of vitamin B6;
   at least 0.00001% w/w of vitamin B12;
   at least 0.01% w/w of zinc;
   at least 20% w/w of L-citrulline;
   at least 10% w/w of the fenugreek seed extract;
   at least 1% w/w of the ATP stimulating component;
   at least 1% w/w of the eurycoma root extract; and
   at least 0.1% w/w of boron.

5. The composition of claim 1, comprising
   from about 0.01% w/w to about 5% w/w of vitamin B6;
   from about 0.00001% w/w to about 1% w/w of vitamin B12;
   from about 0.01% w/w to about 2% w/w of zinc;
   from about 20% w/w to about 75% w/w of the L-citrulline;
   from about 10% w/w to about 50% w/w of the fenugreek seed extract;
   from about 1% w/w to about 20% w/w of the ATP stimulating component;
   from about 1% w/w to about 20% w/w of the eurycoma root extract; and
   from about 0.1% w/w to about 2% w/w of boron.

6. The composition of claim 1, comprising:
   about 0.1% w/w of vitamin B6;
   about 0.0001% w/w of vitamin B12;
   about 0.05% w/w of zinc;
   about 57% w/w of L-citrulline malate;
   about 30% w/w of the fenugreek seed extract;
   about 8% w/w of the ATP stimulating component;
   about 5% w/w of the eurycoma root extract; and
   about 0.5% w/w of boron.

7. The composition of claim 1, comprising:
   about 2 mg of vitamin B6;
   about 0.0024 mg of vitamin B12;
   about 1 mg of zinc;
   about 1125 mg of L-citrulline malate;
   about 600 mg of fenugreek seed extract;
   about 150 mg of an adenosine triphosphate (ATP) stimulating component, comprising:
   ancient peat extract, and
   apple fruit extract;
   about 100 mg eurycoma root extract; and
   about 10 mg boron.

8. A method of increasing free testosterone comprising administering to an individual an effective dose of a composition comprising:
   vitamin B6;
   vitamin B12;
   zinc;
   L-citrulline;
   fenugreek seed extract;
   an adenosine triphosphate (ATP) stimulating component, comprising:
   ancient peat extract, and
   apple fruit extract;
   eurycoma extract; and
   boron.

9. The method of claim 8, wherein the individual is a male human.

10. The method of claim 8, wherein the composition is administered in an oral dosage form.

11. The method of claim 8, wherein the composition increases physical performance in the individual.

12. The method of claim 8, wherein the composition increases the amount of circulating free testosterone.

13. The method of claim 8, wherein the composition increases energy level in the individual.

14. The method of claim 8, wherein the composition increases stamina in the individual.

15. The method of claim 8, wherein the composition increases libido in the individual.

16. The method of claim 8, wherein the composition comprises:
   at least 0.01% w/w of vitamin B6;
   at least 0.00001% w/w of vitamin B12;
   at least 0.01% w/w of zinc;
   at least 20% w/w of L-citrulline;
   at least 10% w/w of the fenugreek seed extract;
   at least 1% w/w of the ATP stimulating component;

at least 1% w/w of the eurycoma root extract; and
at least 0.1% w/w of boron.

17. The method of claim 8, wherein the composition comprises:
from about 0.01% w/w to about 5% w/w of vitamin B6;
from about 0.00001% w/w to about 1% w/w of vitamin B12;
from about 0.01% w/w to about 2% w/w of zinc;
from about 20% w/w to about 75% w/w of the L-citrulline;
from about 10% w/w to about 50% w/w of the fenugreek seed extract;
from about 1% w/w to about 20% w/w of the ATP stimulating component;
from about 1% w/w to about 20% w/w of the eurycoma root extract; and
from about 0.1% w/w to about 2% w/w of boron.

18. The method of claim 8, wherein the composition comprises:
about 0.1% w/w of vitamin B6;
about 0.0001% w/w of vitamin B12;
about 0.05% w/w of zinc;
about 57% w/w of L-citrulline malate;
about 30% w/w of the fenugreek seed extract;
about 8% w/w of the ATP stimulating component;
about 5% w/w of the eurycoma root extract; and
about 0.5% w/w of boron.

19. The method of claim 8, wherein the composition comprises:
about 2 mg of vitamin B6;
about 0.0024 mg of vitamin B12;
about 1 mg of zinc;
about 1125 mg of L-citrulline malate;
about 600 mg of fenugreek seed extract;
about 150 mg of an adenosine triphosphate (ATP) stimulating component, comprising:
ancient peat extract, and
apple fruit extract;
about 100 mg eurycoma root extract; and
about 10 mg boron.

* * * * *